(12) United States Patent
Giacomelli et al.

(10) Patent No.: US 11,028,422 B2
(45) Date of Patent: *Jun. 8, 2021

(54) PROCESS FOR THE PRODUCTION OF ULTRAPURE GALACTO-OLIGOSACCHARIDES

(71) Applicant: Ritter Pharmaceuticals, Inc., Los Angeles, CA (US)

(72) Inventors: Silvia Giacomelli, Sesto Fiorentino (IT); Marco Manoni, Vinci (IT); Giovanni Cipolletti, Milan (IT); Silvia Biagiolini, Arezzo (IT); Luana Vagnoli, Arezzo (IT); Jacopo Chini, Florence (IT)

(73) Assignee: Ritter Pharmaceuticals, Inc., Los Angeles, CA (US)

( * ) Notice: Subject to any disclaimer, the term of this patent is extended or adjusted under 35 U.S.C. 154(b) by 105 days.

This patent is subject to a terminal disclaimer.

(21) Appl. No.: 16/153,544

(22) Filed: Oct. 5, 2018

(65) Prior Publication Data

US 2019/0136280 A1  May 9, 2019

Related U.S. Application Data

(63) Continuation of application No. 14/925,881, filed on Oct. 28, 2015, now abandoned, which is a continuation of application No. 13/388,721, filed as application No. PCT/IB2010/053567 on Aug. 6, 2010, now Pat. No. 9,200,303.

(30) Foreign Application Priority Data

Aug. 7, 2009 (IT) .............. FI2009A000182

(51) Int. Cl.
| | |
|---|---|
| *C12P 19/04* | (2006.01) |
| *A23L 33/21* | (2016.01) |
| *A61K 31/7016* | (2006.01) |
| *A61K 31/702* | (2006.01) |
| *A61K 31/715* | (2006.01) |

(52) U.S. Cl.
CPC .............. *C12P 19/04* (2013.01); *A23L 33/21* (2016.08); *A61K 31/702* (2013.01); *A61K 31/7016* (2013.01); *A61K 31/715* (2013.01); *A23V 2002/00* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 5,149,640 | A | 9/1992 | Oonishi et al. |
| 5,378,833 | A | 1/1995 | Katta et al. |
| 8,591,981 | B2 | 11/2013 | Sprenger et al. |
| 2006/0286258 | A1 | 12/2006 | Petschow et al. |
| 2006/0287276 | A1 | 12/2006 | Rhoades et al. |
| 2007/0274955 | A1 | 11/2007 | Gibson et al. |
| 2009/0092729 | A1 | 4/2009 | Sprenger et al. |
| 2009/0202589 | A1 | 8/2009 | Müller et al. |
| 2010/0035828 | A1 | 2/2010 | M'Rabet et al. |
| 2011/0021417 | A1 | 1/2011 | Rhoades et al. |
| 2011/0189342 | A1 | 8/2011 | Jeong et al. |

FOREIGN PATENT DOCUMENTS

| | | |
|---|---|---|
| CN | 102471792 A | 5/2012 |
| EP | 0272095 A2 | 6/1988 |
| FR | 2723960 | 3/1996 |
| JP | 02-207796 A | 8/1990 |
| WO | WO 2009/113030 | 9/2009 |
| WO | WO 2011/016008 | 2/2011 |

OTHER PUBLICATIONS

Cheng et al.; "Production of high-content galacto-oligosaccharide by enzyme catalysis and fermentation with Kluyveromyces marxianus"; Biotechnol Lett (2006) 28:793-797.

Goulas et al.; Development of a process for the production and purification of x- and β-galacto-oligosaccharides from Bifidobacterium bifidum NCIMB 41171; International Diary Journal 17 (2007) 648-656.

Li et al.; "Production of non-monosaccharide and high-purity galacto-oligosaccharides by immobilized enzyme catalysis and fermentation with immobilized yeast cells"; Process Biochemistry 43 (2008) 896-899.

Maischberger et al.; "Production of lactose-free galacto-oligosaccharide mixtures; comparison of two cellobiose dehydrogenases for the selective oxidation of lactose to lactobionic acid"; Carbohydrate Research 343 (2008) 2140-2147.

Pocedicova et al., J. Food Eng., 99:479-484 (2010).

Shoaf et al.; "Prebiotic Galacto-oligosaccharides Reduce Adherence of Enteropathogenic *Escherichia coli* to Tissue Culture Cells"; Infection and Immunity, Dec. 2006, p. 6920-6928.

Splechtna et al.; "Production of lactose-free galacto-oligosaccharide mixture by using selective enzymatic oxidation of lactose inot lactobionic acid"; Enzyme and Microbial Technology 29 (2001) 434-440.

*Primary Examiner* — Thomas J. Visone (74) *Attorney, Agent, or Firm* — Lewis Kohn & Walker LLP; David M. Kohn (57) ABSTRACT

The present invention describes a process for preparing ultrapure (≥95%) galacto-oligosaccharides (GOS), starting from GOS at lower purities by using sequential microbiological purifications involving *Saccharomyces cerevisiae* and *Streptococcus thermophilus*.

8 Claims, 9 Drawing Sheets

PROCESS FOR THE PRODUCTION OF ULTRAPURE GALACTO-OLIGOSACCHARIDES

FIELD OF THE INVENTION

The present invention relates to the field of preparing high purity (≥95%) galacto-oligosaccharides (GOS), starting from lactose-derived syrups with low GOS content.

STATE OF THE ART

Galacto-oligosaccharides (GOS) consist of a mixture of at least di-, tri-, tetra-, penta- and hexa-saccharides, in which glucose is the free reducing-end sugar and the other sugars in the chain are galactoses linked to each other and to glucose in varying ways depending on the enzyme used in the transglycosylation reaction starting from lactose.

Currently, interest in GOS is steadily growing because recent research has demonstrated the efficiency of these oligosaccharides as prebiotics: in this sense they are a mixture of non-cariogenic non-digestible low-calorie oligosaccharides which stimulate the development of gastrointestinal microflora.

A further benefit of GOS is their anti-adhesive activity: these oligosaccharides can directly inhibit infections caused by enteric pathogens such as E. coli, acting as mimics of the binding sites of pathogens which generally attack gastrointestinal epithelial cells.

Commercially available GOS are synthesized from lactose by using the transglycosylic activity of beta-galactosidases (lactases) isolated from various natural microorganisms (e.g. *Aspergillus oryzae, Penicillium expansum* and *Bacillus circulans*) or modified microorganisms. The GOS structure varies according to the enzyme source. The yield of GOS produced from natural enzymes is generally 20-45% and can be increased by employing recombinant or modified enzymes. The most widely commercially available GOS form contains the GOS at a concentration of about 50-60% by weight and also contains considerable amounts of glucose (by-product of the GOS formation reaction) and non-reacted lactose (starting material). This renders them unusable by people affected by diabetes mellitus or lactose intolerance.

Methods are known in the literature for obtaining high purity GOS, namely those in which all the digestible sugars (lactose, glucose, galactose) are absent. Such methods involve the removal of glucose and lactose in GOS by chromatography, enzymatic oxidation or microbial fermentation. The aforesaid methods however lack large-scale applicability (in the case of chromatography) or present drawbacks.

In Shoaf, K. et al. *Infect. Immun.* 74 (12) 6920-6928, 2006, a mixture containing mono- and disaccharide-free GOS was made in the laboratory by preparative TLC (hence in quantities of a few milligrams).

Splechtna, B. et al. *Enzyme and Microbial Technology* 29 (6) 434-440, 2001 describes the removal of residual lactose by its selective oxidation with fungal cellobiose dehydrogenase into lactobionic acid. This enzyme is not easily available and works by coupling the lactose oxidation with reduction of 2,6-dichloro-indophenol, being present in catalytic concentrations. The oxidized redox mediator is continuously regenerated by the fungal laccase-catalyzed reduction of molecular oxygen into water. Ion exchange chromatographies were used to remove the lactobionic acid.

Cheng, C.-C. et al. *Biotechnol. Lett.* 28 793-797, 2006 describes the removal of residual lactose by fermentation with *Kluyveromyces marxianus*: the process has good yields and leads to a high purity product devoid of glucose, galactose, lactose, but as well as lactose, all other disaccharides present in the GOS mixture prior to treatment with *K. marxianus* are also consumed by the microorganism.

Li, Z. et al. *Process Biochemistry* 2008, 43(8), 896-899 describes the removal of digestible sugars by fermentation with *Saccharomyces cerevisiae* or *Kluyveromyces lactis* immobilized on calcium alginate. The results are good when using *K. lactis*, but unsatisfactory when using *S. cerevisiae*.

The drawback of using *Kluyveromyces marxianus* or *lactis* is that although both are publicly available to the public, they are not commonly employed in the food industry and are therefore not commercially available at low cost in ready-to-use form.

There is an evident need for an alternative method for producing high purity GOS, which is also applicable on an industrial scale and in which all the digestible sugars (lactose, glucose, galactose) are either absent or present in small amounts, and which utilizes easily and widely available microorganisms

DEFINITIONS AND ABBREVIATIONS

GOS=Galacto-oligosaccharides

SUMMARY OF THE INVENTION

The present invention overcomes the aforesaid problem by means of a process for preparing GOS of purity ≥95% in which the overall percentage of the digestible sugars lactose, glucose and galactose is ≤5%, starting from GOS mixtures of a lower purity, said process comprising a fermentation step with *Streptococcus thermophilus* and at least one fermentation step with *Saccharomyces cerevisiae*, where said purity is calculated by any analytical method able to distinguish and quantify GOS and said digestible sugars.

The process enables said digestible sugars to be selectively removed by microbiological purification.

Advantageously said process enables a GOS mixture to be obtained with low contents of the digestible sugars lactose, glucose and galactose, in which not all the disaccharides formed in the transglycosylation are removed by microorganisms.

Advantageously the fermentation step with *S. thermophilus* is found to enable lactose to be selectively removed while preserving other disaccharides which have HPLC retention times very close to that of lactose. This distinctive preservation of the oligosaccharide, identifiable by HPLC with a peak immediately following that of lactose, makes the product obtained by the process different from others known in the art.

The aforesaid process uses low cost commercially available microorganisms widely employed in the food industry; they can be used directly in lyophilized form (the form in which they are purchased) without having to activate them by preparing a pre-fermentation mixture.

The afaoresaid process can be easily applied on an industrial scale, i.e. on a multi-kg scale.

DETAILED DESCRIPTION OF THE INVENTION

In the process of the present invention, any GOS mixture with a purity of <95% can be used as the starting material, most conveniently GOS mixtures with a purity ≥40% being used in which the impurities consist essentially of the digestible sugars lactose, glucose and galactose.

For the purposes of the present invention, to evaluate the purity of the GOS mixtures any HPLC method capable of distinguishing and quantifying GOS, lactose, galactose and glucose is preferably used.

The term "purity" means the area percent by HPLC corresponding to the peaks of said GOS and digestible sugars.

GOS mixtures at 40-60% purity (or higher) are available commercially (e.g. Oligomate 55, Vivinal GOS, Purimune, Cup oligo P) or can be prepared from lactose by transglycosylation catalyzed by a suitable lactase known for the purpose, such as that isolated from *Bacillus circulans*. In particular, the process of the invention is convenient when starting from 40-60% GOS mixtures.

Preferably the process of the invention is such that said fermentation step with *S. thermophilus* is followed by a fermentation step with *S. cerevisiae*. *S. thermophilus* hydrolyses lactose then consumes the glucose produced and accumulates galactose which is then eliminated by *S. cerevisiae*. By means of the fermentation step with *S. thermophilus* the lactose content can be reduced to the desired levels, preferably <5% by HPLC area percent, and more preferably <3%. In case the starting GOS mixture has a glucose content <5% by HPLC area percent, then said process comprises a fermentation step with *S. thermophilus* followed by a fermentation step with *S. cerevisiae*. *S. thermophilus* hydrolyses the lactose then consumes the small amount of glucose initially present and that which it produces during accumulation of galactose, which is then later eliminated by *S. cerevisiae*.

Thus, for example (see example 2), by starting from a commercially available GOS mixture at a purity of about approximately 80% in which glucose is present in a quantity of 2% by HPLC area percent, the lactose content can be reduced by direct fermentation with *S. thermophilus* to the desired levels i.e. <5% by area percent relative to the sum of the area percents of the GOS.

In case the GOS starting mixture has a glucose content by HPLC area percent, the fermentation step with *S. thermophilus* is preceded by a fermentation step with *S. cerevisiae*; in this case the process therefore comprises the following 3 steps:

(a) fermentation with *Saccharomyces cerevisiae*;
(b) fermentation with *Streptococcus thermophilus*;
(c) fermentation with *Saccaromyces cerevisiae*.

Figure 1:
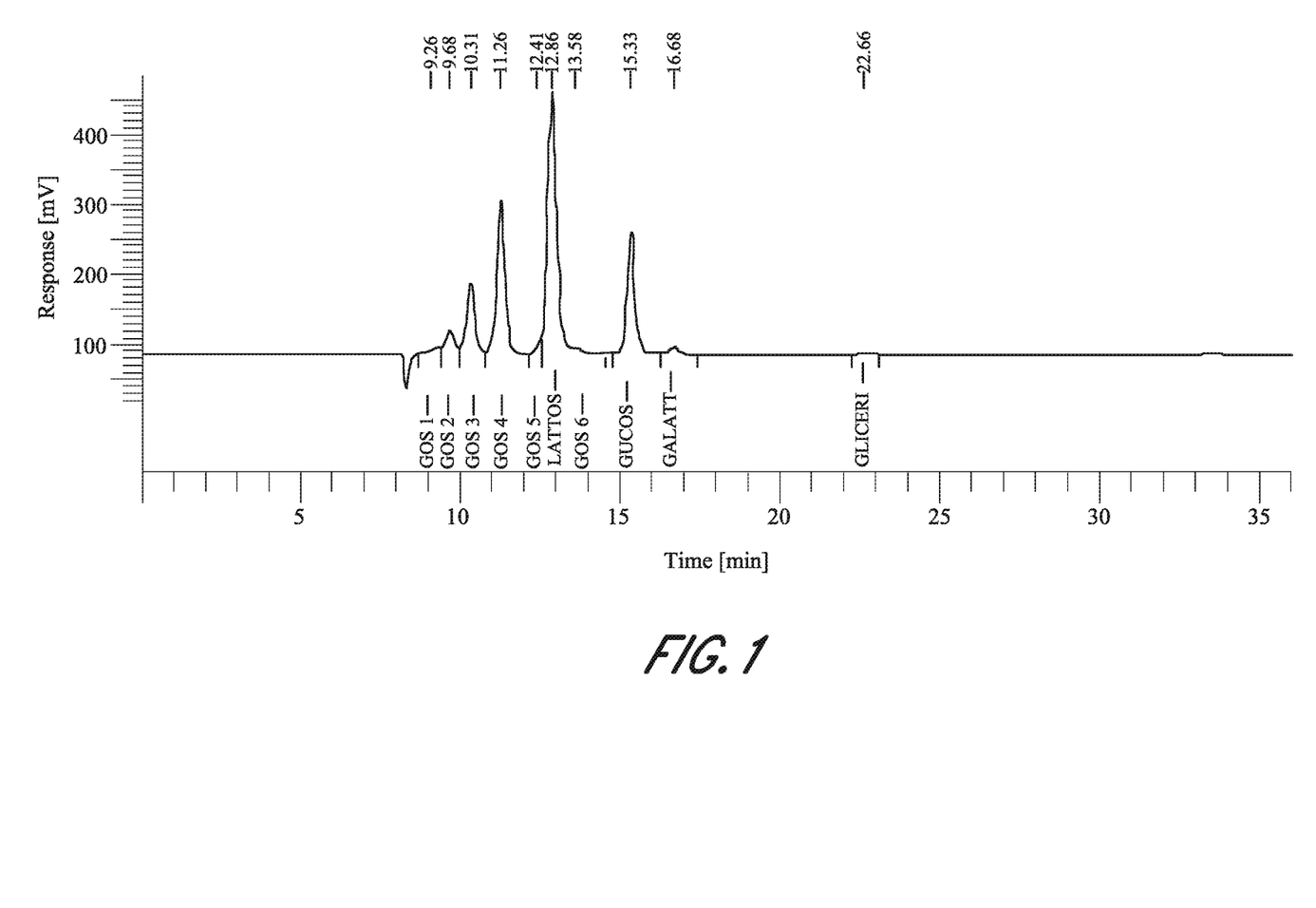
FIG. 1. shows the HPLC trace of a starting GOS sample at 40% purity, of example 1, obtained from lactose by transglycosylation catalyzed by *B. circulans* lactase.
Figure 2:
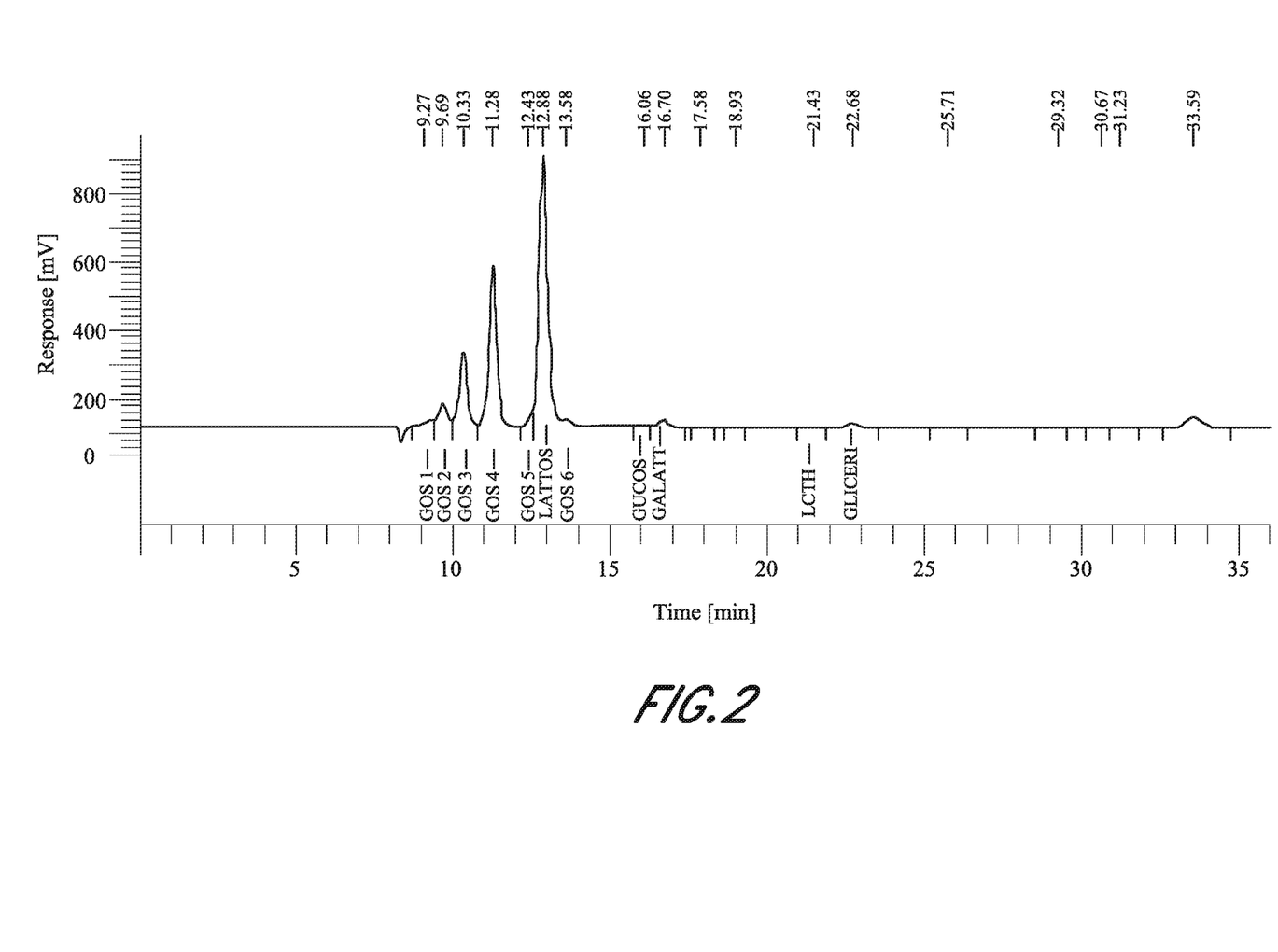
FIG. 2. shows the HPLC trace of a GOS sample, of example 1, after deglucosation with *Saccharomyces cerevisiae* according to the present invention.

Thus, for example (see example 1), when starting from a GOS mixture with a purity of about 40% (see FIG. 1) obtained by transglycosylation with *B. circulans*, fermentation (a) with *S. cerevisiae* enables the glucose present in the starting GOS mixture to be almost completely removed (see FIG. 2.)

Figure 3:
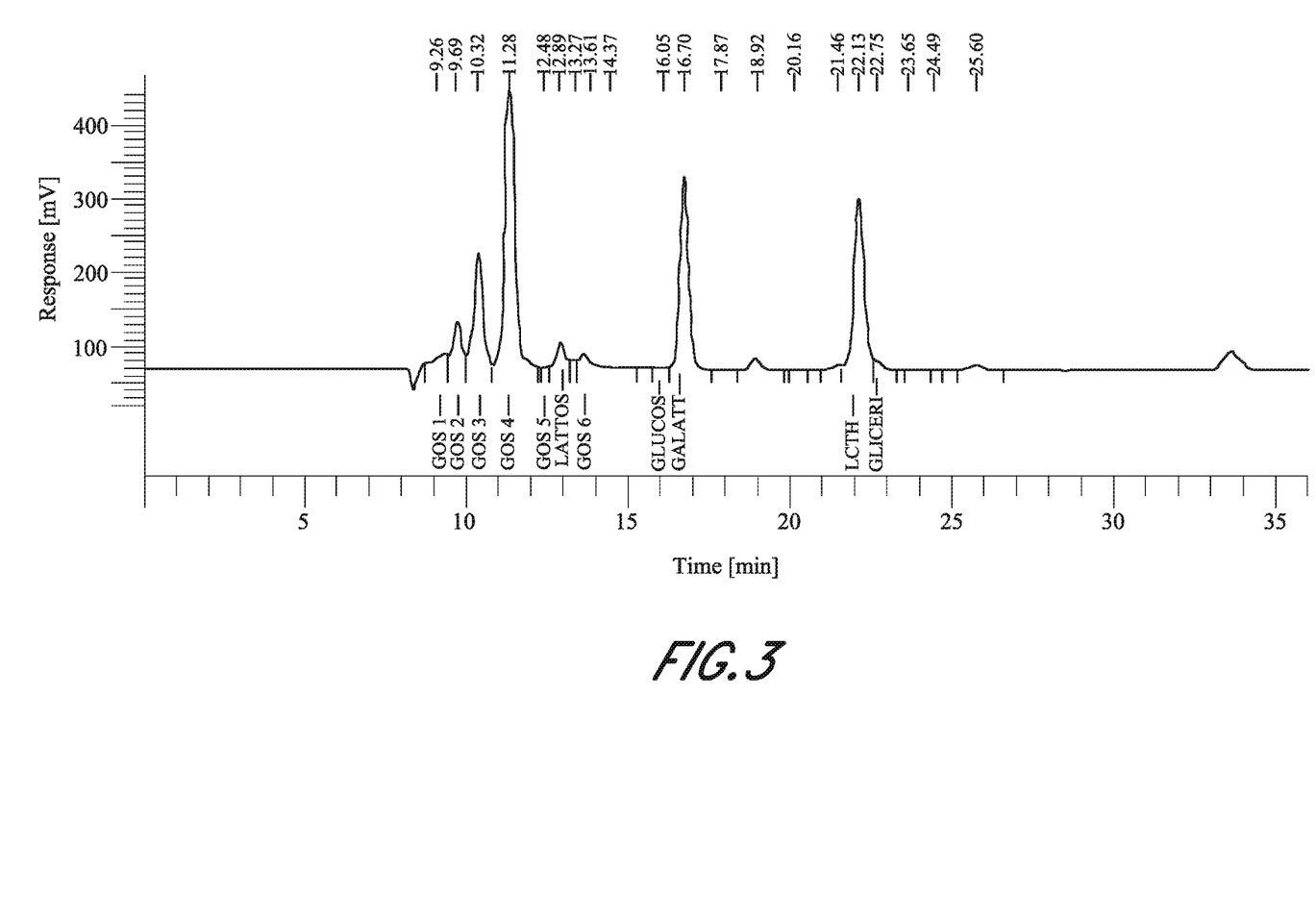
FIG. 3. shows the HPLC trace of a GOS sample, of example 1, after delactosation with *Streptococcus thermophilus* according to the present invention.

Fermentation (b) allows lactose to be lowered to HPLC area percents of less than 3% (see FIG. 3).

It could be seen that when starting with GOS mixtures at 40-60% purity in which glucose is present at a purity of about 20%, if fermentation (b) with *S. thermophilus* is preceded by a deglucosation step such as fermentation (a) then the lactose can be lowered to below 3 area %, whereas direct fermentation with *S. thermophilus* even if prolonged for more than 40 hours, does not enable lactose to be lowered to the desired levels if undertaken without first effecting a deglucosation step (a) with *S. cerevisiae*.

Figure 4A:
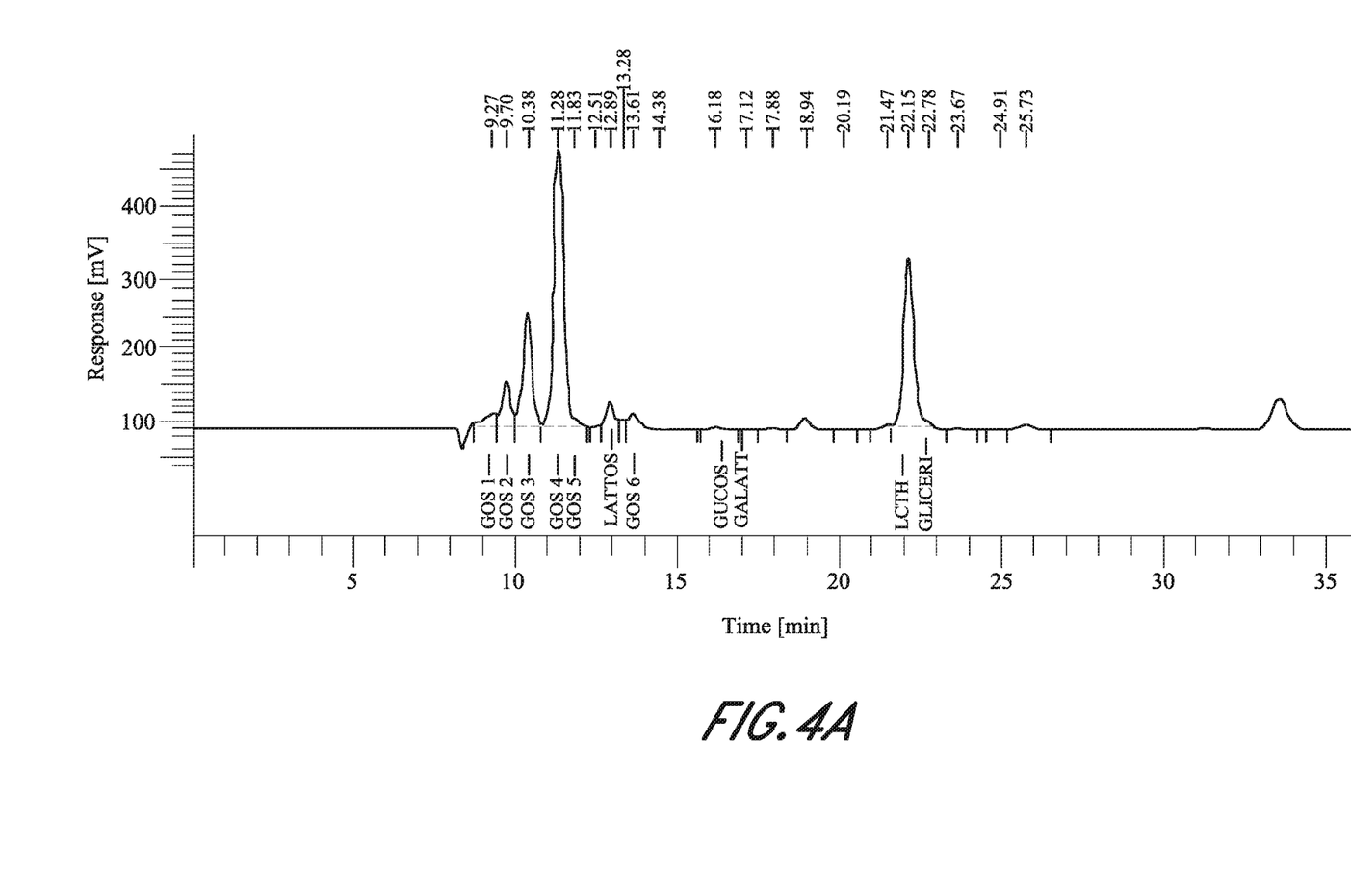
FIG. 4A. shows the HPLC trace of a GOS sample, of example 1, after degalactosation of the sample corresponding to FIG. 3 with *Saccharomyces cerevisiae* according to the present invention after at least 20 hours of fermentation.
Figure 4B:
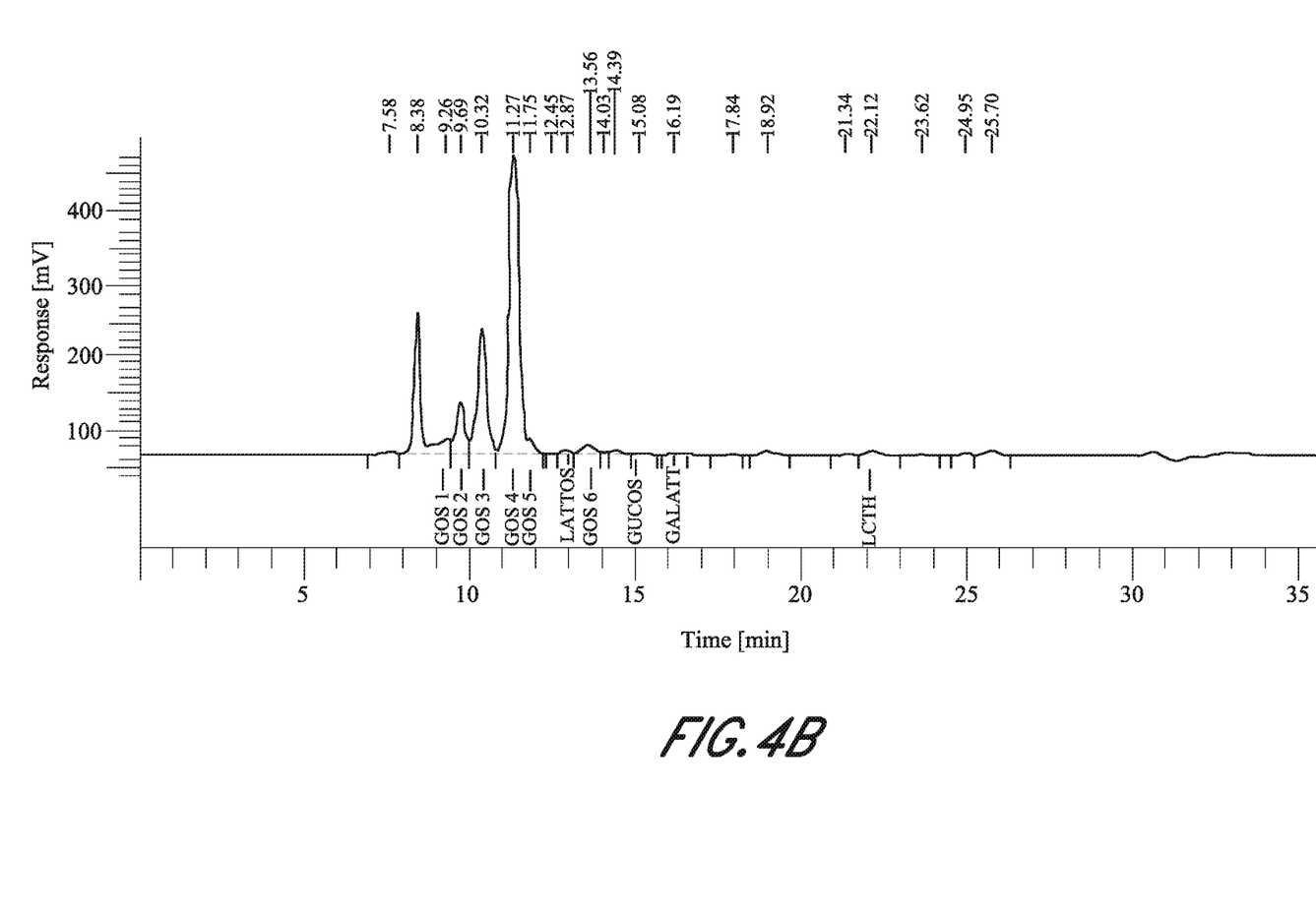
FIG. 4B. shows the HPLC trace of a GOS sample, of example 1, after degalactosation of the sample corresponding to FIG. 3 with *Saccharomyces cerevisiae* according to the present invention B: after at least 40 hours of fermentation.

Fermentation (c) with *S. cerevisiae* allows residual galactose which formed after fermentation with *S. thermophilus* to be almost completely removed (see FIGS. 4A and 4B).

Figure 5:
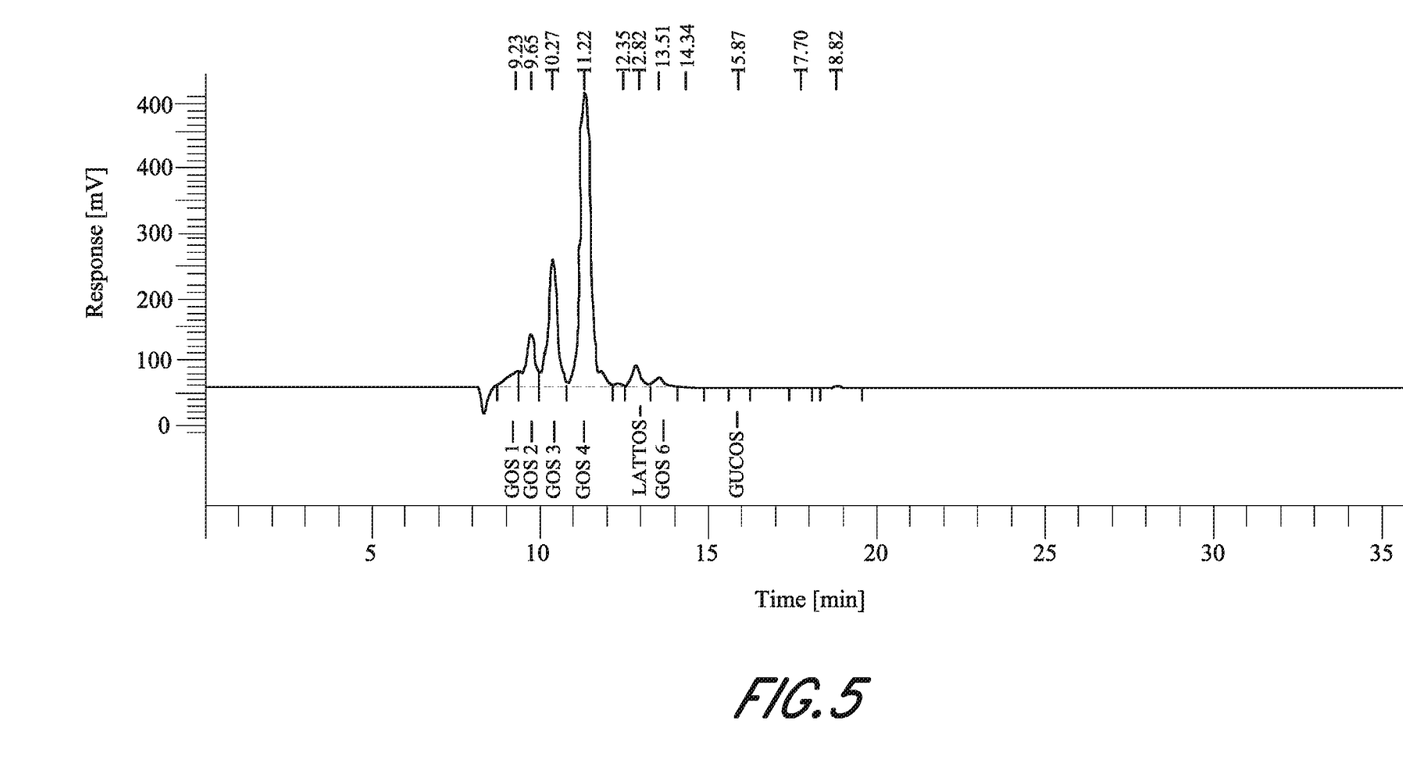
FIG. 5. shows the HPLC trace of a GOS sample with a purity 95% obtained at completion, of example 1, according to the process of the present invention.

At the end of the process, the GOS mixture obtained has a purity of ≥95% in which glucose and galactose if not absent are present in negligible quantities which, together with lactose, nevertheless amount to ≤5% (see FIG. 5).

Fermentations with *S. cerevisiae* are preferably conducted at pH 6.5±0.5 at a temperature of 35±5° C. for at least 12 hours, using 40-15 g of dehydrated *S. cerevisiae* per kg of dry weight of starting GOS. The step (c) can even be conducted for time periods exceeding 40 hours and in such case, a substantial removal of the lactic acid, formed after fermentation (b) with *S. thermophilus*, is actually achieved (see FIG. 4B).

Fermentation with *S. thermophilus* is preferably undertaken at a temperature of 40±5° C., maintaining the pH at 6.0-6.5 by addition of a base, for at least 15 hours and using 1-0.4 g of dehydrated *S. thermophilus* per kg of dry weight of starting GOS.

According to the process of the invention, after the fermentation steps the mixture is preferably subjected to further processing by means of ceramic ultrafiltration, nanofiltration, decolorization with carbon and ion-exchange resin deionization.

According to the process of the invention, the fermentation steps (b) and (c) are preceded by pasteurization, preferably undertaken at 75±5° C. for at least 5 minutes.

In effect, the product obtained at the end of the aforesaid process presents a distinctive GOS profile; during the fermentation step with *S. thermophilus*, lactose is mainly removed, this being evident from the HPLC traces (compare FIG. 2. with FIG. 3, and FIG. 6 with FIG. 7) and it can also be noted that in the disaccharide region there remains a component with a retention time of about 13.6 minutes (indicated as GOS6 in the examples) immediately after the lactose retention time (about 12.9 minutes). Concomitant to the lactose removal, the disappearance of the component with a retention time of about 12.4 minutes (indicated as GOS5 in the examples) can be noted immediately preceding the lactose retention time.

This preservation of the GOS profile is distinctive and is distinguishable from other GOS mixtures known in the state of the art such as those obtained by chromatographic separation or after purification with *Kluyveromyces* genus microorganisms (see example 4 and compare FIG. 1 with FIG. 8), these methods removing indiscriminately all disaccharides present in the GOS mixture.

Therefore the present invention also relates to GOS mixtures obtained from the process i.e. GOS mixtures with a purity ≥95% in which galacto-disaccharides other than lactose are present in quantities ≥1% and the overall percentage of digestible sugars lactose, glucose and galactose is ≤5%.

The aforesaid product, obtained by the process, can be employed for the known purposes including preparation of pharmaceutical compositions, baby formulas and food compositions, these being further aspects of the present invention.

The present invention may be better understood in the light of the following working examples.

Experimental Part
HPLC Method

This is a HPLC method using comparison with an external standard. A HPLC instrument is used with an isocratic pump, an autosampler, a Peltier oven for column temperature control, a refraction index detector and a Transgenomic column ICE-SEP ICE-ION 300, product code ICE-99-9850 equipped with an analogous precolumn. The analyses were carried out under the following working conditions:

Column temperature: 40° C.
Injections: 20 μl
Mobile phase: $H_2SO_4$ 0.015N
Flow rate: 0.4 ml/minute
Analysis time 36 minutes
Integrator: Perkin Elmer Totalchrom Workstation Under the conditions indicated above the retention time of each product was about 12.5 minutes for lactose, 15.0 minutes for glucose, 16.2 minutes for galactose, 21.3 minutes for lactic acid and 22.2 minutes for glycerin (against the external standard).

In the sample solutions, 6 peaks of GOS product were distinguished and identified as:

GOS 1: peak at about 9.3 minutes
GOS 2: peak at about 9.7 minutes
GOS 3: peak at about 10.3 minutes
GOS 4: peak at about 11.3 minutes
GOS 5: peak at about 12.4 minutes
GOS 6: peak at about 13.6 minutes.

In the HPLC tabulation, the terms GOS1-6 simply mean the peaks attributed to GOS, irrespective of the number of saccharide units present therein. The integration system automatically calculated the contents by the formula:

$$\% = A_s \times C_{STD} \times V \times 100 / A_{STD} \times W_s$$

In which:
$A_c$=Area of the peak in the sample solution
$C_{STD}$=Percentage sugar concentration in the standard solution
$W_s$=Sample weight in grams
$A_{STD}$=Area of the sugar peak in the standard solution During process monitoring, the contents of the GOS peaks were not calculated against their own standards but by using the response factor of lactose or by evaluating its purity expressed as area/total area.

Using the analytical method just described, the determination of lactose was invalidated by the possible overlap with other galacto-oligosaccharides.

It is important to note the strong discrepancy found between the determination of lactose in commercial samples using the aforedescribed analytical method and the values provided on the certificates.

For instance, the sample VIVINAL® GOS60 Batch no. 6297770 supplied by Friesland Foods Domo had a certificated lactose content on a dry matter basis of 17.5%, while by HPLC performed in our analytical laboratory the lactose content was 33.2%.

A similar assessment in estimating lactose was found in the Purimune™ sample, Batch no. 20081217 in which the certificated overall purity of the GOS was 90.4%, whereas by HPLC performed in our analytical laboratory (attached) said purity was 83.0% with the purity of lactose being 13.6% by area percent.

The determination of lactose was therefore overestimated by our analytical method, resulting in an exceeding assessment of the lactose concentration present in the final product.

So as not to create ambiguities in the description, in the examples presented hereinafter and in the figures section, only the purity values obtained with the aforedescribed HPLC method are given, as are the values for the commercial products.

EXAMPLE 1

Example of Preparation Starting from Lactose 80 kg of lactose monohydrate (0.22 kmols) were suspended in 120 l of water and heated to 70° C. under mild agitation until the lactose was completely dissolved.

The solution was temperature controlled at 50° C. and the pH adjusted from 5.5 to 5.0 with 27 ml of 75% phosphoric acid.

266 g of lactase from *Bacillus circulans* were added (1500 U/g).

The reaction was monitored by HPLC and after 22 hours the formation of GOS and the appearance of glucose and galactose were detected with a consequent lowering of the lactose area percent purity to less than 40%.

200 kg of a 40% crude GOS solution were obtained, the HPLC trace of which is shown in FIG. 1 and presented in tabular form below:

| Peak # | Delta RT [%] | Time [min] | Component Name | Conc. % | Area [uV*sec] | Response Factor | Amount [Norm. %] | Norm. Area [%] |
|---|---|---|---|---|---|---|---|---|
| 1 | | 9.093 | GOS 1 | 0.309071 | 154704 | 8.6372e+06 | 0.8 | 0.8 |
| 2 | 0.00 | 9.511 | GOS 2 | 1.338322 | 669890 | 8.6372e+06 | 3.5 | 3.5 |
| 3 | | 10.137 | GOS3 | 4.122173 | 2063331 | 8.6372e+06 | 10.6 | 10.7 |
| 4 | 0.75 | 11.082 | GOS4 | 8.925738 | 4467730 | 8.6372e+06 | 23.0 | 23.2 |
| 5 | — | 11.433 | | 5.511e−95 | 31940 | 1.000e+100 | 1e−94 | 0.2 |
| 6 | | 12.247 | GOS5 | 0.414881 | 207666 | 8.6372e+06 | 1.1 | 1.1 |

| Peak # | Delta RT [%] | Time [min] | Component Name | Conc. % | Area [uV*sec] | Response Factor | Amount [Norm. %] | Norm. Area [%] |
|---|---|---|---|---|---|---|---|---|
| 7 | 0.22 | 12.666 | Lattosio | 15.240043 | 7628321 | 8.6372e+06 | 39.3 | 39.6 |
| 8 | | 13.372 | GOS6 | 0.471197 | 235855 | 8.6372e+06 | 1.2 | 1.2 |
| 9 | 0.05 | 15.131 | Glucosio | 7.519908 | 3601195 | 8.2635e+06 | 19.4 | 18.7 |
| 10 | 0.07 | 16.431 | Galattosio | 0.395477 | 190570 | 8.3150e+06 | 1.0 | 1.0 |
| 11 | — | 17.629 | | 3.856e−96 | 2235 | 1.000e+100 | 1e−95 | 0.0 |
| 12 | 0.16 | 21.766 | LCTH | 0.003749 | 1173 | 5.3962e+06 | 0.0 | 0.0 |
| 13 | | 22.328 | Glicerina | 0.015260 | 6177 | 6.9847e+06 | 0.0 | 0.0 |
| | | | | 38.755819 | 19260786 | 2.000e+100 | 100.0 | 100.0 |

STEP 1—Deglucosation with *S. cerevisiae*

The aforestated starting mixture was acidified to pH 3.0 with 250 ml of 75% phosphoric acid: under these pH conditions preservation at ambient temperature was possible.

46 kg of 40% crude GOS solution (Batch no. 014491N9) were diluted with 140 l of water and temperature controlled at 37° C. After adjusting the solution pH from pH 2.8 to pH 7.0 with 600 ml of 24% ammonia, 200 g of lyophilized brewer's yeast were added. The deglucosation step, monitored by HPLC, was complete after 24 hours of vigorous agitation.

The mixture was pasteurized at 70° C. for about 5 minutes then temperature controlled at 40° C.

FIG. 2 shows the HPLC trace of the mixture after pasteurization, presented below in tabular form.

| Peak # | Delta RT [%] | Time [min] | Component Name | Conc. % | Area [uV*sec] | Response Factor | Amount [Norm. %] | Norm. Area [%] |
|---|---|---|---|---|---|---|---|---|
| 1 | 2.62 | 9.275 | GOS 1 | 0.095989 | 402093 | 8.7961e+06 | 1.2 | 1.2 |
| 2 | 0.16 | 9.694 | GOS 2 | 0.358713 | 1502624 | 8.7961e+06 | 4.4 | 4.3 |
| 3 | | 10.329 | GOS3 | 1.074666 | 4501696 | 8.7961e+06 | 13.3 | 12.9 |
| 4 | 2.36 | 11.284 | GOS4 | 2.277114 | 9538665 | 8.7961e+06 | 28.2 | 27.4 |
| 5 | 0.00 | 12.432 | GOS5 | 0.105556 | 442165 | 8.7961e+06 | 1.3 | 1.3 |
| 6 | 0.31 | 12.882 | Lattosio | 3.842640 | 16096537 | 8.7961e+06 | 47.6 | 46.2 |
| 7 | 0.48 | 13.585 | GOS6 | 0.127645 | 534696 | 8.7961e+06 | 1.6 | 1.5 |
| 8 | 4.14 | 16.059 | Glucosio | 0.004367 | 17492 | 8.4113e+06 | 0.1 | 0.1 |
| 9 | | 16.697 | Galattosio | 0.082239 | 329174 | 8.4049e+06 | 1.0 | 0.9 |
| 10 | — | 17.882 | | 3.713e−96 | 17680 | 1.000e+100 | 5e−95 | 0.1 |
| 11 | — | 18.925 | | 1.129e−96 | 5378 | 1.000e+100 | 1e−95 | 0.0 |
| 12 | | 21.431 | LCTH | 0.020144 | 51870 | 5.4069e+06 | 0.2 | 0.1 |
| 13 | | 22.683 | Glicerina | 0.086023 | 280713 | 6.8522e+06 | 1.1 | 0.8 |
| 14 | — | 25.713 | | 1.111e−95 | 52902 | 1.000e+100 | 1e−94 | 0.2 |
| 15 | — | 29.315 | | 1.650e−96 | 7859 | 1.000e+100 | 2e−95 | 0.0 |
| 16 | — | 30.666 | | 4.041e−96 | 19245 | 1.000e+100 | 5e−95 | 0.1 |
| 17 | — | 31.229 | | 4.144e−96 | 19734 | 1.000e+100 | 5e−95 | 0.1 |
| 18 | — | 33.589 | | 2.158e−94 | 1027592 | 1.000e+100 | 3e−93 | 2.9 |
| | | | | 8.075096 | 34848113 | 7.000e+100 | 100.0 | 100.0 |

STEP 2—Delactosation with *S. thermophilus*

2.5 g/l of yeast extract were added to the above mixture (resulting from step 1) and the pH was adjusted from pH 5.2 to pH 6.6 with 400 ml of 15% sodium hydroxide. The mixture was inoculated with 5 g of *Streptococcus thermophilus*: fermentation proceeded at pH 6.4-6.5 by adding 15% sodium hydroxide by means of a pH-stat. The end of the reaction, monitored by HPLC, was reached after 26 hours when the lactose content in the mixture was less than 3 area %.

The mixture was pasteurized at 70° C. for about 5 minutes then temperature controlled at 37° C.

FIG. 3 shows the HPLC trace of the mixture after pasteurization, presented below in tabular form.

| Peak # | Delta RT [%] | Time [min] | Component Name | Conc. % | Area [uV*sec] | Response Factor | Amount [Norm. %] | Norm. Area [%] |
|---|---|---|---|---|---|---|---|---|
| 1 | 1.42 | 9.257 | GOS 1 | 0.089800 | 306895 | 8.8584e+06 | 1.3 | 1.4 |
| 2 | 0.14 | 9.692 | GOS 2 | 0.296940 | 1014808 | 8.8584e+06 | 4.2 | 4.7 |
| 3 | | 10.324 | GOS3 | 0.792435 | 2708190 | 8.8584e+06 | 11.1 | 12.4 |
| 4 | 1.62 | 11.277 | GOS4 | 1.907072 | 6517527 | 8.8584e+06 | 26.7 | 30.0 |
| 5 | — | 12.477 | | 2.801e−96 | 10806 | 1.000e+100 | 4e−95 | 0.0 |

-continued

| Peak # | Delta RT [%] | Time [min] | Component Name | Conc. % | Area [uV*sec] | Response Factor | Amount [Norm. %] | Norm. Area [%] |
|---|---|---|---|---|---|---|---|---|
| 6 | | 12.889 | Lattosio | 0.163174 | 557655 | 8.8584e+06 | 2.3 | 2.6 |
| 7 | — | 13.268 | | 3.809e−95 | 146969 | 1.000e+100 | 5e−94 | 0.7 |
| 8 | 0.68 | 13.612 | GOS6 | 0.114462 | 391180 | 8.8584e+06 | 1.6 | 1.8 |
| 9 | — | 14.374 | | 1.105e−95 | 42639 | 1.000e+100 | 2e−94 | 0.2 |
| 10 | 4.21 | 16.051 | Glucosio | 0.007876 | 25635 | 8.4366e+06 | 0.1 | 0.1 |
| 11 | | 16.701 | Galattosio | 1.324742 | 4362275 | 8.5353e+06 | 18.5 | 20.1 |
| 12 | — | 17.870 | | 1.276e−95 | 49224 | 1.000e+100 | 2e−94 | 0.2 |
| 13 | — | 18.923 | | 6.937e−95 | 267628 | 1.000e+100 | 1e−93 | 1.2 |
| 14 | — | 20.163 | | 6.679e−97 | 2577 | 1.000e+100 | 9e−96 | 0.0 |
| 15 | — | 21.459 | LCTH | 1.524e−95 | 59474 | 1.000e+100 | 2e−94 | 0.3 |
| 16 | | 22.127 | Glicerina | 2.375647 | 4931565 | 5.3807e+06 | 33.2 | 22.7 |
| 17 | 0.07 | 22.746 | | 0.077039 | 203886 | 6.8599e+06 | 1.1 | 0.9 |
| 18 | — | 23.647 | | 1.215e−95 | 46875 | 1.000e+100 | 2e−94 | 0.2 |
| 19 | — | 24.491 | | 2.779e−97 | 1072 | 1.000e+100 | 4e−96 | 0.0 |
| 20 | — | 25.801 | | 2.805e−95 | 108218 | 1.000e+100 | 4e−94 | 0.5 |
| | | | | 7.149186 | 21755103 | 1.000e+101 | 100.0 | 100.0 |

STEP 3—Degalactosation with *S. cerevisiae*

200 g of lyophilized brewer's yeast were added to the mixture resulting from step 2: after 20 hours of vigorous agitation the degalactosation step, monitored by HPLC, was complete.

The reaction was stopped by adding 5 l of 50% sulphuric acid until pH 3.0 was reached.

FIGS. 4A and 4B show the HPLC trace of the mixture after degalactosation, presented below in tabular form.

| Peak # | Delta RT [%] | Time [min] | Component Name | Conc. % | Area [uV*sec] | Response Factor | Amount [Norm. %] | Norm. Area [%] |
|---|---|---|---|---|---|---|---|---|
| 1 | 1.57 | 9.270 | GOS 1 | 0.097962 | 358655 | 8.7717e+06 | 1.6 | 1.8 |
| 2 | 0.18 | 9.696 | GOS 2 | 0.312481 | 1144050 | 8.7717e+06 | 5.1 | 5.8 |
| 3 | | 10.328 | GOS3 | 0.827617 | 3030055 | 8.7717e+06 | 13.5 | 15.4 |
| 4 | 1.66 | 11.282 | GOS4 | 1.968015 | 7205257 | 8.7717e+06 | 32.0 | 36.7 |
| 5 | | 11.827 | GOS5 | 0.018272 | 66898 | 8.7717e+06 | 0.3 | 0.3 |
| 6 | — | 12.508 | | 3.997e−95 | 16683 | 1.000e+100 | 6e−95 | 0.1 |
| 7 | | 12.894 | Lattosio | 0.157271 | 575796 | 8.7717e+06 | 2.6 | 2.9 |
| 8 | — | 13.276 | | 3.002e−95 | 125300 | 1.000e+100 | 5e−94 | 0.6 |
| 9 | 0.68 | 13.613 | GOS6 | 0.153856 | 563296 | 8.7717e+06 | 2.5 | 2.9 |
| 10 | — | 14.381 | | 1.490e−95 | 62185 | 1.000e+100 | 2e−94 | 0.3 |
| 11 | 4.96 | 16.177 | Glucosio | 0.021663 | 75309 | 8.3290e+06 | 0.4 | 0.4 |
| 12 | 2.15 | 17.117 | Galattosio | 0.001645 | 5858 | 8.5330e+06 | 0.0 | 0.0 |
| 13 | — | 17.881 | | 1.395e−05 | 58207 | 1.000e+100 | 2e−94 | 0.3 |
| 14 | — | 18.936 | | 6.927e−95 | 289128 | 1.000e+100 | 1e−93 | 1.5 |
| 15 | — | 20.187 | | 1.127e−96 | 4705 | 1.000e+100 | 2e−95 | 0.0 |
| 16 | — | 21.466 | | 2.285e−95 | 95358 | 1.000e+100 | 4e−94 | 0.5 |
| 17 | | 22.147 | LCTH | 2.528752 | 5590606 | 5.2968e+06 | 41.1 | 28.5 |
| 18 | 0.17 | 22.776 | Glicerina | 0.061780 | 174711 | 6.7754e+06 | 1.0 | 0.9 |
| 19 | — | 23.668 | | 8.130e−96 | 33932 | 1.000e+100 | 1e−94 | 0.2 |
| 20 | — | 24.907 | | 8.769e−97 | 3660 | 1.000e+100 | 1e−95 | 0.0 |
| 21 | — | 25.733 | | 3.543e−95 | 147894 | 1.000e+100 | 6e−94 | 0.8 |
| | | | | 6.149314 | 19627543 | 1.000e+101 | 100.0 | 100.0 |

The mixture was clarified by removing the cells by ultrafiltration.

The low molecular weight fermentation by-products (lactic acid, glycerin etc.) were then removed by nanofiltration.

The solution was then decolorized over carbon, desalinated with a pair of ion-exchange resins, namely a strong cationic (Amberlite C-200 H⁺ form, 3 l) and a weak anionic (IRA-96 free base form, 3 l), arranged in series.

The demineralised solution was then microfiltered and concentrated under vacuum until a saccharometric concentration of 75° Brix was attained.

9 kg of a GOS mixture were obtained with a purity ≥95%; the HPLC trace of the GOS mixture obtained at the end of the process is shown in FIG. 5, presented below in tabular form.

| Peak # | Delta RT [%] | Time [min] | Component Name | Conc. % | Area [uV*sec] | Response Factor | Amount [Norm. %] | Norm. Area [%] |
|---|---|---|---|---|---|---|---|---|
| 1 |  | 9.228 | GOS1 | 1.828791 | 418901 | 8.5581e+06 | 2.7 | 2.6 |
| 2 |  | 9.648 | GOS2 | 6.640325 | 1521025 | 8.5581e+06 | 9.7 | 9.6 |
| 3 |  | 10.274 | GOS3 | 17.010960 | 3896510 | 8.5581e+06 | 24.8 | 24.5 |
| 4 | 2.13 | 11.222 | GOS4 | 39.207543 | 8980833 | 8.5581e+06 | 57.1 | 56.6 |
| 5 | — | 12.351 |  | 2.085e−94 | 55794 | 1.000e+100 | 3e−94 | 0.4 |
| 6 | 0.23 | 12.819 | Lattosio | 2.769118 | 634291 | 8.5581e+06 | 4.0 | 4.0 |
| 7 |  | 13.511 | GOS6 | 1.233729 | 282596 | 8.5581e+06 | 1.8 | 1.8 |
| 8 | — | 14.335 |  | 5.725e−95 | 15322 | 1.000e+100 | 8e−95 | 0.1 |
| 9 | 3.83 | 15.869 | Glucosio | 0.031758 | 7003 | 8.2394e+06 | 0.0 | 0.0 |
| 10 | — | 17.703 |  | 1.500e−95 | 4014 | 1.000e+100 | 2e−95 | 0.0 |
| 11 | — | 18.822 |  | 2.397e−94 | 64148 | 1.000e+100 | 3e−94 | 0.4 |
|  |  |  |  | 68.722223 | 15880437 | 4.000e+100 | 100.0 | 100.0 |

From the tabulated data and the attached chromatograms of the various steps, it can be seen that during step 2 (fermentation with *S. thermophilus*) the GOS5 peak disappears, while the GOS6 peak remains more or less unaltered.

Table 1 presents a summary of the results of the various steps in example 1:

TABLE 1

Figure 6:
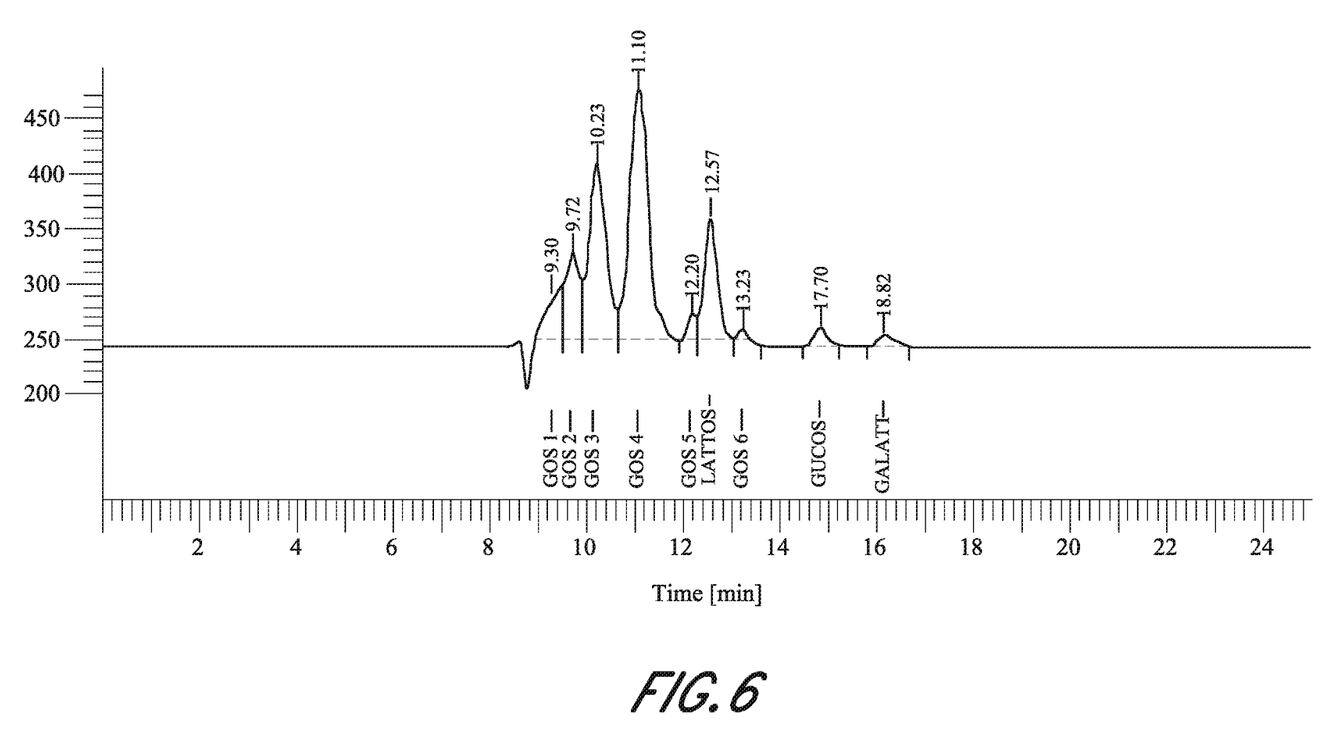
FIG. 6. shows the HPLC trace of a starting GOS sample, of example 2, namely Purimune™ (GO-P90) purchased from GTC Nutrition, Golden, Colo., USA.
Figure 7:
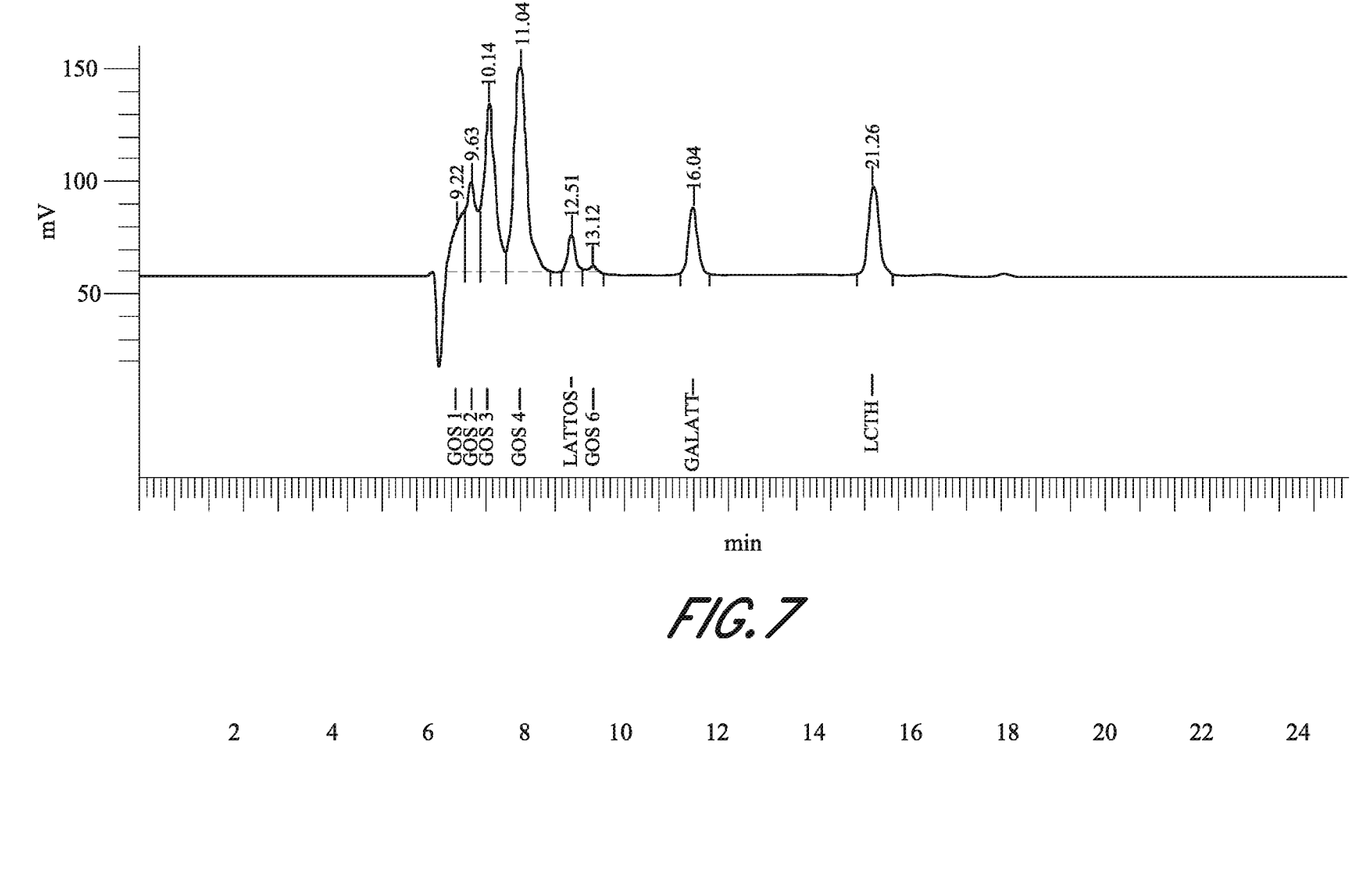
FIG. 7. shows the HPLC trace of a GOS sample with a purity ≥95%, obtained at completion, of example 2, according to the process of the present invention.

| EX 1 |  | GOS | LAC-TOSE | GLU-COSE | GALAC-TOSE |
|---|---|---|---|---|---|
| START | % CONC | 15.6 | 15.24 | 7.52 | 0.4 |
|  | % PURITY | 40.5 | 39.6 | 18.7 | 1 |
|  | RELATIVE | 40.6 | 39.7 | 18.7 | 1 |
| STEP 1 | % CONC | 4 | 3.83 | 0 | 0.09 |
| (fermentation with | % PURITY | 48.3 | 46.3 | 0 | 1 |
| *S. cerevisiae*) | RELATIVE | 50.5 | 48.4 | 0 | 1 |
| STEP 2 | % CONC | 3.13 | 0.18 | 0.01 | 1.29 |
| (fermentation with | % PURITY | 50 | 2.8 | 0.1 | 20.1 |
| *S. thermophilus*) | RELATIVE | 68.5 | 3.8 | 0.1 | 27.5 |
| STEP 3 | % CONC | 3.38 | 0.16 | 0.02 | 0 |
| (fermentation with | % PURITY | 62.9 | 2.9 | 0.4 | 0 |
| *S. cerevisiae*) | RELATIVE | 95 | 4.4 | 0.6 | 0 |
| FINAL PRODUCT | % CONC | 66.2 | 2.78 | 0.03 | n.d. |
|  | % PURITY | 95.5 | 4 | 0 | n.d. |
|  | RELATIVE | 96 | 4 | 0 | n.d. | in which: % CONC = concentration in weight/weight %
% PURITY = area percent subtended by the HPLC peak RELATIVE % = purity of GOS/Σ purity of GOS, lactose, glucose and galactose
EXAMPLE 2—Example of preparation starting from GOS at 83% (90% commercial) 200 g of Purimune GOS (GO - P90) Batch no. 20081217 were solubilized in 1800 ml of water. FIG. 6 shows the chromatogram and the solution HPLC is presented below in tabular form.

5 g/l of yeast extract were added and the pH adjusted from pH 4.9 to pH 6.4 with 0.3 ml of 15% sodium hydroxide. Following inoculation with 75 mg of *Streptococcus thermophilus*, the fermentation proceeded at pH 6.3-6.5 by adding 15% sodium hydroxide by means of a pH-stat. The end of the reaction, monitored by HPLC, was reached after 15 hours when the lactose content of the mixture was less than 5% by area percent relative to the sum of the area percents of GOS.

A summary of the results obtained are presented in table 2.

TABLE 2

| EX 2 |  | GOS | LAC-TOSE | GLU-COSE | GALAC-TOSE |
|---|---|---|---|---|---|
| START | % CONC | 7.03 | 1.14 | 0.16 | 0.14 |
|  | % PURITY | 83.1 | 13.5 | 1.8 | 1.5 |
|  | RELATIVE | 83.1 | 13.5 | 1.8 | 1.5 |
| STEP 1 | % CONC | 6.07 | 0.28 | 0 | 1.39 |
| (fermentation with | % PURITY | 78 | 3.6 | 0 | 7 |
| *S. thermophilus*) | RELATIVE | 88 | 4 | 0 | 7.9 |

Abbreviations:

% CONC=concentration in weight/weight %

% PURITY=area percent subtended by the HPLC peak

RELATIVE %=purity of GOS/Σ purity of GOS, lactose, glucose and galactose

| Peak # | Time [min] | Component Name | Conc. % | Area [μN · s] | Response factor | Amount norm. % | Area Norm. [%] |
|---|---|---|---|---|---|---|---|
| 1 | 9.181 | GOS1 | 0.494174 | 209703 | 8.3152e+06 | 5.8 | 5.8 |
| 2 | 9.562 | GOS2 | 0.833452 | 353676 | 8.3152e+06 | 9.8 | 9.9 |
| 3 | 10.072 | GOS3 | 2.055456 | 872234 | 8.3152e+06 | 24.3 | 24.3 |
| 4 | 10.951 | GOS4 | 3.297243 | 1399187 | 8.3152e+06 | 39.0 | 39.0 |
| 5 | 12.044 | GOS5 | 0.202695 | 86014 | 8.3152e+06 | 2.4 | 2.4 |
| 6 | 12.428 | Lattosio | 1.144282 | 485577 | 8.3152e+06 | 13.5 | 13.5 |
| 7 | 13.041 | GOS6 | 0.142975 | 60672 | 8.3152e+06 | 1.7 | 1.7 |
| 8 | 14.735 | Glucosio | 0.155892 | 62950 | 7.9126e+06 | 1.8 | 1.8 |
| 9 | 15.993 | Galattosio | 0.136621 | 54958 | 7.8825e+06 | 1.6 | 1.5 |
| 10 | 28.904 |  | 7.133e−97 | 364 | 1.000e+100 | 8e−96 | 0.0 |
|  |  |  | 8.462789 | 3585334 |  | 100.0 | 100.0 |

The glucose present has an area percent of <5% hence the procedure continued directly with fermentation by lactic acid bacteria culture.

The experiment was stopped at this stage, but it was clear that the mixture could be subsequently degalactosated and purified in the manner already described in example 1.

Direct fermentation with *Streptococcus thermophilus*, thus avoiding deglucosation with *S. cerevisiae* which in this case was superfluous, resulted in the desired area ratio of GOS to lactose. Moreover, considering that the subsequent fermentation with *S. cerevisiae* was able to remove galactose, a GOS purity of 95.6% relative to the lactose alone can theoretically be calculated based on the area percent values reported in table 2.

EXAMPLE 3

Example of Preparation Starting from GOS at 43% (60% Commercial)

427 g of Vivinal Gos60 Batch no. 6297770 were solubilized in 1600 ml of water: the HPLC data of the solution is presented below in tabular form:

| Peak # | Time [min] | Component Name | Conc. % | Area [µV · s] | Response factor | Amount norm. % | Area Norm. [%] |
|---|---|---|---|---|---|---|---|
| 1 | 9.365 | GOS1 | 0.132997 | 117776 | 8.4830e+06 | 1.4 | 1.4 |
| 2 | 9.710 | GOS2 | 0.386673 | 342420 | 8.4830e+06 | 4.0 | 4.1 |
| 3 | 10.230 | GOS3 | 0.978558 | 866565 | 8.4830e+06 | 10.2 | 10.3 |
| 4 | 11.086 | GOS4 | 2.153239 | 1906809 | 8.4830e+06 | 22.3 | 22.7 |
| 5 | 12.198 | GOS5 | 0.283797 | 251318 | 8.4830e+06 | 2.9 | 3.0 |
| 6 | 12.556 | Lattosio | 3.315665 | 2936200 | 8.4830e+06 | 34.4 | 34.9 |
| 7 | 13.186 | GOS6 | 0.153348 | 135798 | 8.4830e+06 | 1.6 | 1.6 |
| 8 | 14.855 | Glucosio | 2.070889 | 1719196 | 7.9525e+06 | 21.5 | 20.4 |
| 9 | 16.122 | Galattosio | 0.160862 | 137854 | 8.2093e+06 | 1.7 | 1.6 |
|  |  |  | 9.636028 | 8413937 |  | 100.0 | 100.0 |

The procedure was carried out exactly as in example 1, with the first deglucosation step with *S. cerevisiae* followed by fermentation with *S. thermophilus*; at the end of this step (step 2 in Ex. 1) an HPLC was obtained and the result, being absolutely comparable to that of Example 1, is tabulated below:

| Peak # | Time [min] | Component Name | Conc. % | Area [µV · s] | Response factor | Amount norm. % | Area Norm. [%] |
|---|---|---|---|---|---|---|---|
| 1 | 9.265 | GOS1 | 0.103310 | 93473 | 8.4830e+06 | 1.4 | 1.6 |
| 2 | 9.641 | GOS2 | 0.382881 | 346426 | 8.4830e+06 | 5.3 | 6.1 |
| 3 | 10.163 | GOS3 | 0.908611 | 822101 | 8.4830e+06 | 12.6 | 14.5 |
| 4 | 11.025 | GOS4 | 1.991562 | 1801941 | 8.4830e+06 | 27.6 | 31.7 |
| 5 | 12.104 |  | 4.315e−96 | 12100 | 1.000e+100 | 7e−95 | 0.2 |
| 6 | 12.498 | Lattosio | 0.167432 | 151490 | 8.4830e+06 | 2.3 | 2.7 |
| 7 | 13.124 | GOS6 | 0.145504 | 144421 | 8.4830e+06 | 2.0 | 2.5 |
| 8 | 14.788 | Glucosio | 0.005412 | 4590 | 7.9525e+06 | 0.1 | 0.1 |
| 9 | 16.048 | Galattosio | 1.003410 | 878581 | 8.2093e+06 | 13.9 | 15.4 |
| 10 | 21.841 | LCTH | 2.387452 | 1342275 | 5.2712e+06 | 33.1 | 23.6 |
| 11 | 21.841 | GlOH | 0.125566 | 89471 | 6.6806e+06 | 1.7 | 1.6 |
|  |  |  | 7.221140 | 5686869 |  | 100.0 | 100.0 |

It can also be seen in this example that the GOS5 peak disappears during fermentation with *S. thermophilus*, while the GOS6 peak remains more or less unaltered.

As in example 2, this experiment was stopped at this stage and the mixture was degalactosated and purified in the manner already described in example 1.

Moreover, considering that the second fermentation with *S. cerevisiae* was able to remove galactose, a GOS purity of 95.2% relative to the lactose alone can theoretically be calculated based on the area percent values reported in the table for the second HPLC of this example.

EXAMPLE 4

Example of Preparation Starting from GOS at 40% with *K. marxianus* (Chem, C.-C.; et al. *Biotechnol. Lett.* 28 793-797, 2006)

The strain *K. marxianus* ATCC 56497 was cultured on a plate containing autoclave-sterilized YPD medium with agar for yeasts, and placed in an incubator at 30° C. for 48 hours.

To prepare the pre-fermentation mixture, 100 ml of liquid YPD medium were prepared, autoclave-sterilized then inoculated with the colonies picked up from the previously prepared plate. The microorganisms were grown in a shaker at a temperature of 30° C. and shaken at 200 rpm for 24 hours.

The test was carried out on the same starting solution as Example 1: 460 g of a 40% crude GOS solution (Batch no. 014491N9) diluted with 1.4 l of water.

After adjusting the solution pH from pH 2.8 to pH 5.4 with 15% sodium hydroxide, it was temperature controlled at 30° C.

Figure 8:
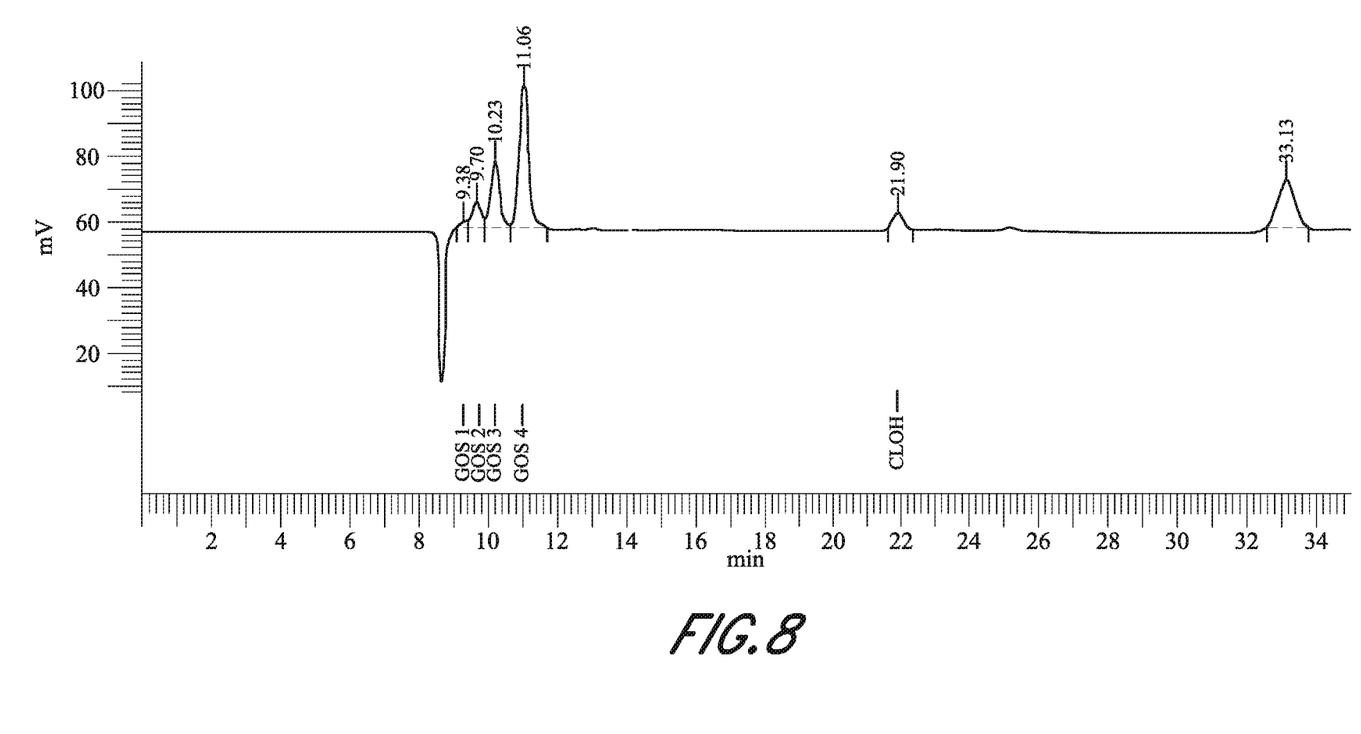
FIG. 8. shows the HPLC trace of a GOS sample of example 4, obtained after fermentation with *Kluveromyces marxianus*.

The entire pre-fermentation mixture was used for the inoculation. The fermentation proceeded at pH 5.2-5.4 by adding 15% sodium hydroxide by means of a pH-stat. Sampling of the mixture was carried out after 48 hours and shows the reaction to have reached completion, as can be seen from the tabulated HPLC data (see also FIG. 8) presented below:

| Peak # | Time [min] | Component Name | Conc. % | Area [µV · s] | Response factor | Amount norm. % | Area Norm. [%] |
|---|---|---|---|---|---|---|---|
| 1 | 9.382 | GOS1 | 0.070000 | 29745 | 8.5106e+06 | 1.9 | 1.5 |
| 2 | 9.700 | GOS2 | 0.355858 | 151213 | 8.5106e+06 | 9.7 | 7.6 |
| 3 | 10.232 | GOS3 | 0.944881 | 401505 | 8.5106e+06 | 25.9 | 20.0 |
| 4 | 11.065 | GOS4 | 1.989309 | 845311 | 8.5106e+06 | 54.5 | 42.2 |
| 5 | 21.900 | GlOH | 0.289913 | 96941 | 6.6971e+06 | 7.9 | 4.8 |
| 6 | 33.135 | | 9.570e−94 | 477834 | 1.000e+100 | 3e−92 | 23.9 |
| | | | 3.649961 | 2002549 | | 100.0 | 100.0 |

The reaction effectively resulted in the almost complete disappearance of lactose, but it should be noted from the attached chromatogram (FIG. 8) that peaks attributable to the galacto-oligosaccharides are absent from the entire disaccharide region (between 12.2 min and 13.2 min).

The invention claimed is:

1. A method of purifying a galactooligosaccharides (GOS) composition with a purity ≥95% in which an overall percentage of the digestible sugars lactose, glucose and galactose is ≤5%, comprising providing a GOS mixture of a lower purity and subjecting the GOS mixture to at least one fermentation step with *Streptococcus thermophilus* and at least one fermentation step with *Saccharomyces cerevisiae*, where said purity is calculated by any analytical method able to distinguish and quantify GOS and said digestible sugars.

2. The method of claim 1, wherein said method comprises a fermentation step with *S. thermophilus* followed by a fermentation step with *S. cerevisiae*.

3. The method of claim 1, wherein said method comprises a fermentation step with *S. thermophilus* followed by a fermentation step with *S. cerevisiae* when a starting GOS mixture has a glucose ≤5% by HPLC area percent.

4. The method of claim 2, wherein the fermentation step with *S. thermophilus* is preceded by a fermentation step with *S. cerevisiae* comprises when the starting GOS mixture has a glucose content >5% by HPLC area percent.

5. The method of claim 4, wherein the fermentations with *S. cerevisiae* are conducted at pH 6.5±0.5 at a temperature of 35±5° C. for at least 12 hours using 15-40 g of dehydrated *S. cerevisiae* per kg of dry weight of starting GOS.

6. The method of claim 5 wherein the fermentation with *S. thermophilus* is conducted at a temperature of 40±5° C. maintaining the pH at 6.0-6.5 by adding a base, for at least 15 hours and using 1-0.4 g of dehydrated *S. thermophiles* per kg of dry weight of starting GOS.

7. The method prepared of claim 6 wherein after the fermentation steps the mixture is subjected to further processing by means of ceramic ultrafiltration, nanofiltration, decolorization with carbon and ion-exchange resin deionization.

8. The method of claim 1, wherein said fermentation steps are preceded by pasteurization undertaken at 75±5° C. for at least 5 minutes.

* * * * *

UNITED STATES PATENT AND TRADEMARK OFFICE
CERTIFICATE OF CORRECTION

PATENT NO. : 11,028,422 B2
APPLICATION NO. : 16/153544
DATED : June 8, 2021
INVENTOR(S) : Giacomelli et al.

Page 1 of 1

It is certified that error appears in the above-identified patent and that said Letters Patent is hereby corrected as shown below:

In the Specification

Column 3, Line 27: "Kluveromyces" should read "Kluyveromyces"

Column 4, Line 15: "Saccaromyces" should read "Saccharomyces"

Signed and Sealed this
Third Day of August, 2021

Drew Hirshfeld
*Performing the Functions and Duties of the
Under Secretary of Commerce for Intellectual Property and
Director of the United States Patent and Trademark Office*